(12) United States Patent
Vuori et al.

(10) Patent No.: US 9,125,404 B2
(45) Date of Patent: Sep. 8, 2015

(54) BIOCIDAL COMPOSITION FOR WOOD, METHOD FOR WOOD TREATMENT, AND WOOD PRODUCED THEREBY

(75) Inventors: Antti Vuori, Helsinki (FI); Timo Nissinen, Ylöjärvi (FI)

(73) Assignee: TMAINCO FINLAND (FI)

( * ) Notice: Subject to any disclaimer, the term of this patent is extended or adjusted under 35 U.S.C. 154(b) by 520 days.

(21) Appl. No.: 13/381,280

(22) PCT Filed: Jul. 14, 2009

(86) PCT No.: PCT/FI2009/050625
§ 371 (c)(1),
(2), (4) Date: Mar. 5, 2012

(87) PCT Pub. No.: WO2011/007043
PCT Pub. Date: Jan. 20, 2011

(65) Prior Publication Data
US 2012/0156517 A1    Jun. 21, 2012

(51) Int. Cl.
| | | |
|---|---|---|
| *B05D 1/18* | (2006.01) | |
| *A01N 37/12* | (2006.01) | |
| *C08H 8/00* | (2010.01) | |
| *B27K 3/34* | (2006.01) | |
| *B27K 3/50* | (2006.01) | |
| *C08K 5/103* | (2006.01) | |

(52) U.S. Cl.
CPC ....... *A01N 37/12* (2013.01); *C08H 8/00* (2013.01); *B27K 3/346* (2013.01); *B27K 3/50* (2013.01); *C08K 5/103* (2013.01); *Y10T 428/662* (2014.04)

(58) Field of Classification Search
CPC .................................... B27K 3/34; B27K 3/16
USPC ........................................................ 427/440
See application file for complete search history.

(56) References Cited

U.S. PATENT DOCUMENTS

| | | | |
|---|---|---|---|
| 2,045,350 A | | 6/1936 | Griffin et al. |
| 2,429,643 A | * | 10/1947 | Pratt ................................. 8/121 |
| 7,300,705 B2 | * | 11/2007 | Neogi et al. .................. 428/532 |

FOREIGN PATENT DOCUMENTS

| | | |
|---|---|---|
| DE | 199873 C | 1/1907 |
| DE | 19618210 A1 | 11/1997 |
| DE | 102006008843 A1 | 8/2007 |
| GB | 275641 A | 1/1929 |
| GB | 743401 A | 1/1956 |
| GB | 891579 A | 3/1962 |
| WO | 2009071745 A2 | 6/2009 |

OTHER PUBLICATIONS

The International Search Report and Written Opinion dated Aug. 13, 2010.
The International Preliminary Report on Patentability dated Oct. 12, 2011.
The Written Opinion of the International Preliminary Examining Authority dated Jun. 15, 2011.
Filak, M., et al., "Water-Soluble Flameproofing Impregnating Agent for Wood," Cpalus, 1982, XP002958410.
Chwalbe, C.G., Berling K., "New Cheap Fire-Protecting Material for Wood," Caplus, 1932, XP002958409.

* cited by examiner

*Primary Examiner* — David Turocy
(74) *Attorney, Agent, or Firm* — Thomas Horstemeyer, LLP

(57) ABSTRACT

The invention relates to a method for treating wood in order to improve its properties of use and storage, and to thus obtained treated wood product. In the method the wood to be treated is contacted with a treatment composition comprising monoester, diester or triester or a mixture thereof formed by a water soluble $C_1$-$C_{10}$ alcohol and formic acid as an equilibrium solution. In addition, the invention relates to specific treatment solution compositions.

20 Claims, No Drawings

BIOCIDAL COMPOSITION FOR WOOD, METHOD FOR WOOD TREATMENT, AND WOOD PRODUCED THEREBY

CROSS REFERENCE TO RELATED APPLICATION

This application is the 35 U.S.C. §371 national stage of PCT application entitled "Biocidal Composition for Wood, Method for Wood Treatment, and Wood Produced Thereby," having serial number PCT/FI2009/050625, filed on 14 Jul. 2009, which is incorporated by reference in its entirety.

The invention relates to a method for treating wood with the formate ester of formic acid in order to improve the durability of wood and the thus obtained treated wood product. In addition the invention relates to compositions suitable for this purpose.

In Europe wood material is expensive and thus elevation of the degree of refining is widely considered as the only option in the field in order to assure growth or at least preservation at the present level of business. Prevention of biological decay of wood and improvement of the fire and water resistances are known to be sectors where the refining value of wood should particularly be elevated. As an example, one of the significant obstacles for using wood as construction material is fire safety. On many markets, for instance in Japan, it would also be preferable for wood to retain its normal original colour as long as possible. Darkening of wood due to sunlight and humidity is considered to be architecturally unaesthetical, said darkening thus contributing to the reduction of the use of wood in the construction industry.

Microbes of wood are often divided into two groups according to their enzymatic activities and decomposition abilities. The first group consists of fungi assimilating contents of dead plant cells without decomposing the lignified cell wall of wood cells. Said fungi include moulds and blue stain fungi. Brown and white rot fungi are some of the most efficient decomposing fungi in this group, but also Actinobacteria and Ascomycetes fungi are able to decompose lignified cell wall of wood cells. In addition, many insects, such as termites, make use of wood material for nourishment.

Attempts have been made in order to improve the properties of wood material, such as its durability, endurance and appearance in various environmental surroundings, in various ways, traditionally by making use of toxic heavy metal based impregnating agents. The requirement of the treated wood being environmentally friendly and non-toxic has brought about treating wood with a plurality of other less harmful ways, such as drying by applying heat, methylating, acetylating, furfurylating, alkylating, treating wood with resins and polymers or by applying less harmful treatments with salts or acids.

Formic acid and especially its formate salts have been used successfully and in an environmentally friendly way for this purpose. Formate contained in the wood material has been found to diminish essentially problems encountered in using wood material.

From the previous disclosure of the applicant, WO 2009/071745, one is familiar with a composition for treating wood that accomplishes at the same time several of the required and desirable qualities. The composition is safe for its user and environmentally minimally burdening (harmless), it is well absorbed or impregnated in all different wood materials, and it will be retained by the wood without significantly washing out. Moreover it protects wood against both rot and blue stain fungi and also against dimensional changes, cracking and changes in colour. Furthermore it improves the fire resistance of wood and is not harmful to the consistency of wood after the treatment, even in long-term use. In said composition there are present at least one $C_1$-$C_7$ monocarboxylic acid or any salt thereof or mixtures thereof, such as formic acid or formate, and at least one chelating agent, such as for instance ethylenediaminesuccinic acid (EDDS), iminodisuccinic acid (ISA), N-bis-[2-(1,2-dicarboxyetoxy)ethyl]aspartic acid (AES) or 1-hydroxyethylidene-1,1-diphosphonic acid (HEDP), in solution in a liquid, water based vehicle. The wood product treated with the present composition is well suited for many differing and demanding circumstances of use, and several preferred qualities are fulfilled simultaneously. Especially with said composition wood material is obtained that simultaneously has good decay resistance, good fire resistance and a good stability regarding colour.

References in application WO 2009/071745 describe also carboxylic acid and salt based compositions intended for use in various other wood protection applications and methods in general.

In addition to the above described qualities it would be desirable that the treating composition be fully retained in the wood after the treatment. It should not be washed out of the wood composition in its eventual end point of use in even optionally stringent environmental circumstances, such as e.g. in contact with damp soil. Moreover protection is typically needed for long-term use in various environmental surroundings.

By chemically modifying wood one has been able to improve the properties of dimensional stability and biological durability of wood products. Acetylation of the wood product has been regarded as an outstanding method considering the end product, that is, the treated wood product. The process of acetylation was developed as early as in the nineteen twenties and it is one of the most common and well-studied methods of treatment. The acetylation of wood is traditionally carried out using acetic anhydride, whereby the hydroxyl groups present in the hygroscopic components of wood are esterified and acetic acid is produced as a by-product. The properties of acetylated wood and products made thereof depend for instance in addition to the reaction conditions, such as temperature and reaction time, on catalyst and by-product residues contained in the wood.

Swelling and shrinking of the acetylated wood are diminished and resistance to decay and against insects is improved as the acetylation acts as a biocide of decaying fungi and insects of wood. In addition it improves the abrasion resistance and hardness of wood.

However, it has been noted that an acetylation treatment may change the colour of those wood types that naturally carry reddish tones. Moreover acetylation may lead to poor adhesiveness with traditional adhesives. However, the main problem with acetylation is the susceptibility to water of the acetic anhydride used that makes the treatment process technically complex and as a result thereof quite expensive. It is difficult to combine the process as part of the rest of the already existing treatment process of sawn timber. Moreover the acetyl groups contained in acetylated wood will hydrolyze slowly under the influence of moisture as a result of which the acetyl content of the treated wood gradually diminishes whereby upon release of acetic acid the corrosion of fastening devices, such as nails and screws, will increase. Also the smell of the acetic acid formed in the hydrolysis reaction is quite strong, which is unpleasant from the viewpoint of the user. Accordingly, by a long-term exposition, as the acetyl groups hydrolyze, the dimensional stability and protective properties against decay are gradually diminished.

In the application US 2006083910 acetylated wood is produced by reacting dried wood containing 2-15% by weight of detained moisture with isopropenyl acetate at the temperature of 50-125° C. in the presence of 0.02-2% by weight of an acid catalyst either in liquid or vapour phase. The wood product obtained from the treatment was dried at the temperature of 80-125° C. and the pressure of 0.1-1 bar. The boiling point of isopropenyl acetate is low and its industrial handling is problematic due to the properties of this compound.

The object of the present invention is to provide a wood product the usability and storage properties of which are good and which is environmentally friendly.

Furthermore the second object is to provide a process which is technically easy and swift to carry out in order to produce a wood product the usability and storage qualities of which are good and which is environmentally friendly.

BRIEF DESCRIPTION OF THE INVENTION

For attaining the inventive goals the wood is treated as presented in claim 1. In addition, the invention provides the compositions for treating wood according to claims 7-9. The invention presents also the treated wood product according to claim 11.

In making the present invention it was surprisingly found out that a composition containing formate ester of formic acid is useful for effective protection of wood. Thereby excellent usability, storage, durability and appearance qualities are obtained for a wood product that is treated with said composition. At the same time it was noted that the formate contained in the composition is efficiently and at high concentration detained in the structure of the wood product and is not washed out thereof even in long-term use.

With the composition used according to this invention containing formate ester of formic acid, preferably as glyceryl formate, for treatment of wood one is able to produce wood that is equivalent with CCA impregnated wood, i.e. even the highest wood protection class 1 may be achieved therewith. In addition, the composition makes it possible for the treated wood material to be included in fire control class B which is the highest possible class for wood.

It was noted that the composition according to the invention was able to inhibit efficiently the growth of both mould and blue stain fungi and decay of wood. In addition, it keeps pest insects at bay and significantly increases the fire resistance of wood. Furthermore the composition is able to prevent dimensional changes of wood and its cracking during storage and long-term use plus it contributes to the preservation of the original colour of the material to be treated. The hydrophobicity of a wood product treated with this composition is improved while the hydrophilic hydroxyl groups of wood are efficiently and permanently esterified.

DETAILED DESCRIPTION OF THE INVENTION

The term "wood" or "wood material" is used for all materials and products that contain harvested and processed raw timber and that are suitable for the production of wood based structures and that typically aim at treating to maintain and improve the original wooden qualities thereof. These include specifically composite structures containing harvested and processed raw timber, such as combination products of wood and plastic, and products made of purely harvested or processed raw timber, such as sawn timber, wooden construction materials such as wood-plastic combination products, and products produced from purely containing harvested and processed raw timber, such as sawn timber, wooden construction materials and elements, chipped and unchipped planks and various wood products upgraded thereof, such as round logs, planks and laths. Additionally elements may be included in wood, such as plates, e.g. chipboard, plywood board or LVL products (Laminated Veneer Lumber). The wood to be treated can also be as finished structures which may be treated as such with well-known methods of treatment and equipment according to the invention, such as panels, plaques, wall elements and like construction materials, furniture, outdoor furniture and other wooden objects.

It is preferred that the wood according to the invention is harvested and processed raw timber or wood products that may if needed be, e.g. submerged or pressure impregnated chemically in order to uphold and improve the original qualities of wood. It is preferred that the wood is sawn timber or wood products refined thereof.

In the method according to the invention wood is contacted with a composition for treating wood that comprises monoester, diester or triester or any mixture thereof of a water soluble $C_1$-$C_{19}$ alcohol and formic acid as an equilibrium solution.

When mixing together formic acid and water soluble $C_1$-$C_{10}$ alcohol a monoester, diester or triester or an equilibrium solution of the mixture thereof is produced as reaction product. Depending on the reaction conditions, such as the amounts of water and formic acid present, respectively, the compound produced contains its starting materials and reaction products in a certain equilibrium state typical for this mixture.

The composition for treating wood according to the invention comprises an ester product of water soluble $C_1$-$C_{10}$ alcohol and formic acid, such as for instance monovalent alcohols, methanol, ethanol, propanol, butanol, pentanol, hexanol or derivatives thereof, or multivalent, such as divalent or trivalent alcohols. It is preferred that the alcohol is a water soluble $C_2$-$C_7$ alcohol. With esters formed with higher alcohols the water solubility decreases and as to the esters produced of lower alcohols, the transesterification decreases. More preferred is that the alcohol is multivalent, aliphatic, water soluble $C_2$-$C_5$ alcohol, such as dioles and trioles. Most preferred is that the alcohol is glycerol, ethylene glycol or propylene glycol, especially glycerol. As solute the composition contains essentially water, preferably purified water.

Glyceryl formate can be made with well-known methods, for instance according to patent application DE199873. Glyceryl formate in its various forms or equilibrium mixtures is not sensitive e.g. to the moisture contained in air, and its water solubility is good. Compositions made thereof are easy and simple to handle and use even in industrial scale. All the references cited in this specification are incorporated in the description of the invention by reference.

According to a preferred embodiment of the invention the glyceryl formate used in the composition for treatment is prepared by mixing slowly together the amount of formic acid needed, preferably in a stoichiometric excess of 25-50% by weight, in the glycerol at ambient temperatures where after the temperature is raised to be the equivalent of distillation temperature, over 100° C., preferably 130-140° C. and most preferred about 140° C., and the water and excess formic acid are distillated out of the mixture. It is preferred that the distillation is performed at decreased pressures whereby even the distillation temperatures are lower than when distillating at ambient pressures, respectively. The formic acid content of the ester product formed can if needed be further decreased by on-going distillation in the presence of any generally known distillation auxiliary agent, such as diisopropyl ether. The glyceryl formate thus obtained is a mixture of mono, di and triformates. The substitution level is preferably 1.0-3.0, more preferred is about 1.5-2.0 and most preferred is 1.8-2.0. When esterifying glycerol with formic acid, principally five different compounds in thermodynamic equilibrium are obtained, glyceryl-1-monoformate (CAS 2203-62 5), glyceryl-2-monoformate, glyceryl-1,3-diformate (CAS 10303-53-4), glyceryl-1,2-diformate and glyceryl-1,2,3-triformate (CAS 32765-69-8). Due to the fact that the esterification reaction favours, however, carbons one and three of the glycerol molecule only minor amounts of 2-monoformate and 1,2-diformate are produced. The equilibrium can be manipulated by removing water and acid.

A man skilled in the art is able to prepare glyceryl formate also by other well-known means, the same applying to other equivalent formic acid esters according to the invention.

The final concentration of formate in the wood product and also preferably formylation is influenced by the substitution level of the composition used; the higher the substitution level, the higher is the activity of the composition.

According to another embodiment of the composition for treating wood that is used in the present invention the ester is in a concentrated state. The ester, preferably glyceryl ester is as a concentrated balanced solution the composition of which is over 85% by weight, preferably 78-99% by weight, more preferred is 78-89% by weight, of glyceryl ester, 1-2% by weight, preferably 1-1.5% by weight glycerol and 1-20% by weight, preferably 1-10% by weight, free formic acid, the remainder being water while the substitution level of the ester is preferably 1.8-2.0, more preferably around 1.9, for instance for shipping and/or storage purposes. As a concentrated solution the storage properties of the solution are good. It is preferred that the substitution is decreased below 10%, more preferably below 5%, in long-term storage over several months. The concentrate may, if needed, be diluted to a desired concentration of use, preferably at the point of use and with water before the wood is contacted with the treating composition.

According to another embodiment the concentration to be used in the invention, preferably the concentration of use of the equilibrium solution of glyceryl formate, is 1-100% by weight, preferably 1-50% by weight, more preferably 1-30% by weight. Especially when using pressure impregnation weaker solutions might come in to question, whereas compositions of higher concentration may be used for surface treatments.

According to one preferred embodiment according to the invention the composition for treatment contains 78-90% by weight glyceryl formate, 1-15% by weight of free formic acid, the remainder being glycerol and water.

In addition to the ester formed by the reaction of water-soluble $C_1$-$C_{10}$ alcohol and formic acid, the treating composition can contain any suitable component that pre-serves the structural properties of wood. It is preferred that the treating composition contains in addition a chelating agent, more preferably a chelating agent that is essentially biodegradable, and is more preferably ethylenediaminesuccinic acid (EDDS), iminodisuccinic acid (ISA), any derivatives of aspartic acid, such as N-bis[2-(1,2-dicarboxyetoxy)ethyl]aspartic acid (AES) of phosphonic acid or a salt thereof, such as 1-hydroxy ethylidene-1,1-diphosphonic acid (HEDP); $C_2$-$C_7$ monocarboxylic acid, more preferred are acetic acid, propionic acid, sorbic acid, benzoic acid; a salt of $C_1$-$C_7$ monocarboxylic acid, more preferably alkaline metal, alkaline earth or ammonium salts. If needed, this salt can also be prepared in or ex situ by neutralizing a suitable compound for forming the salt. E.g. an ammonium salt may be prepared also by neutralizing acid to produce the salt. It is preferred that the cation in the salt is sodium, potassium, magnesium, calcium and/or ammonium or mixtures thereof. The anion in the salt is preferably formate and/or sorbate, the antibacterial efficiency of which is good and solubility in water is sufficient. More preferably the salt is sodium, potassium, calcium or ammonium salt of formate or sorbate or a mixture thereof. In the composition of treatment according to the present invention further a fixing agent and/or agents for making it more hydrophobic may be present. The fixing agents in question can be fatty acids, paraffins, polymers, such as polyethene or derivatives thereof, such as oxidized polyethene, starch, cellulose or derivatives thereof, chitosan, esters, waxes, such as Montane waxes including purified montane (C26-C32) acids and/or esters thereof, amide waxes, such as oxazoline based waxes, sparingly soluble formates or silicon compounds, such as silanes, siloxanes or silicones. Agents for rendering the composition more hydrophobic may be resins or derivatives thereof, surface adhesives, e.g. alkylketenedimer (AKD) or alkenylsuccinic acid (ASA) and tall oil or derivatives thereof. It is preferred that as agents rendering the composition more hydrophobic AKD, ASA and/or tall oil, more preferably in an amount of 0.01-5.0% by weight are used. The addition of AKD, ASA or tall oil specifically hinders the washing out of wood the optional chelating agent or its salt and/or monocarboxylic acid or its salt.

An additional organic biocide is not necessarily needed because the formate contained in the treating solution used according to the invention remains efficiently in the structure of treated wood and acts even such as a compound that inhibits the function of bacteria. However, if one wishes to use a separate biocide in order to combat the microbes more efficiently, an organic biocide can be added to the composition, such as e.g. iodopropa-2-nyle-N-butylcarbamate (IPBC), polyhexamethylene guanidinium (PHMG) compounds, such as chloride or sulphate salts thereof, propiconazole or other equivalent compounds. Preferably the organic biocide added is IPBC, PHMG and/or propiconazole. Preferably the organic biocide added is used in an amount of 0.01-5.0% by weight, more preferably 0.01-1.0% by weight, in order to counteract the growth of mould and blue stain fungi. Thereby is obtained a durable product for a long-term mould burden (standard EN130).

The form of the treating composition used according to the invention is liquid and fluid and it can be brought at least partly into the wood by various methods. The fluidity of the composition may be adjusted if needed with additives known in the art, such as with carboxy-methyl cellulose (CMC).

According to the invention the treatment composition used can also contain different additives, depending on the application in question. If it is intended that the composition is used for producing colour, colouring agents can be added thereto, such as organic colouring agents, preferably 1-80 weight %, or pigments, preferably 1-85 weight %, especially if for the wood surface treated even visual change like painting is desired. For instance CMC can be used as a binding agent that acts even as a rheological auxiliary agent. The pigments and organic dyes are preferably free from heavy metals. As pigments use can be made of e.g. well-known iron oxide pigments.

In the method according to the invention formate is fixed to the wood to be treated, preferably the wood is formylated by contacting it with some composition for treatment described above.

The composition for treatment can be brought into contact with the wood to be treated by any suitable well-known procedure. It is preferred that the treating composition is contacted with the wood to be treated by impregnating with it the wood to be treated thoroughly and to a certain depth from surface, for instance, by impregnating, submerging, spraying, vaporization (atomization) or by spreading. Due to the various options the treatment can be accomplished in context with other wood treatments at a suitable stage, such as for instance by final drying of wood. The physical properties of the composition, e.g. viscosity, may be adjusted according to means of treatment and as needed.

The treating composition used according to the invention can be heated, and/or elevated temperatures may be used in the method, still improving impregnation of the treating composition into the wood. Use of lowered or increased pressures known from traditional CCA-impregnation also improves impregnation. In the inventive method the treating composition can be used in all the various ways by which wood is customarily impregnated, such as pressure treatment. The environmentally friendly composition offers, however, a plurality of other options for instance in wood construction and indoors building that have not been feasible with more toxic agents.

The method according to the invention is particularly well suited for process treatments where a good, up to the heart of wood penetrating ability, such as impregnation, is required. The composition can be forced into the wood as is known by a pressure treatment impregnation process in which to begin with, the wood is kept at lowered pressures for water removal from its inner parts after which the composition is brought into contact with wood and the penetration into the wood is accelerated by elevated pressures.

The method of treatment according to the invention makes possible an environmentally friendly, simple, efficient and inexpensive way for treating wood materials, which method is easy to implement into other present treatment stages as part of an already existing process. The method can be one part of treatment stages of wood material or wooden objects that comprise successive stages without causing major changes in treatment line assemblies.

The composition used according to the invention is suitable for treatment of both processed wood and raw timber, and this can be accomplished either in storage places of wood or separately in a treatment plant meant for timber products whereby the treating composition and wood may be contacted with each other in many different ways. The method is also well suited for protection of finished structures.

The method according to the invention is suitable even for targets that are not exclusively of wood, but composites of wood and some other material. It is required that the treatment is subjected only to the wooden parts of the target.

According to one preferred embodiment the wood to be treated is formylated with a treatment composition that contains monoester, diester or triester formed by $C_1$-$C_{10}$ aliphatic alcohol and formic acid, preferably glyceryl formate as an equilibrium solution in that the formylation comprises at least the following steps:

First the wood to be treated is dried, preferably at temperatures of 10-110° C. and/or reduced pressures that enhance the drying process. If needed, the wood is dried in a way that its equilibrium moisture is according to the circumstances, preferably below 30% by weight, more preferably below 20% by weight depending on the temperature and moisture content of the surrounding air. The wood is dried in a way that the water contained therein is eliminated efficiently enough for the treatment to succeed and to be enhanced.

Next, the treating composition used according to the invention is contacted with the wood to be treated. It is preferred that this takes place at elevated temperatures and/or elevated pressures. The conditions of the treatment composition are similar to the typical impregnation processes. More preferably the elevated pressure is above 5 bar, more preferably 7 bar. More preferably the effect of the treatment composition is enhanced and the formylation rate of the treated wood is improved by increasing the temperature of the treatment, preferably to more than 90° C., more preferably to 100-110° C. The time spent for treatment should be long enough for the transesterification to take place. Mass transfer is restricted by diffusion, similarly to traditional CCA treatments, for instance. The time of treatment is at least half an hour, more preferably at least one hour, most preferably is at least two hours.

After this the wood is dried, preferably at an elevated temperature and/or at reduced pressure. After-drying may be a one-stage or multistage process, wherein by applying reduced pressure and optionally elevated drying temperatures, preferably over 90° C., more preferably 100-110° C., the water absorbed in the structure can be removed and also the free formic acid is eliminated.

If the treating solution used is diluted, it must be contacted with the wood to be treated preferably within less than 10 h from dilution, more preferably less than 5 h. A dilute water solution such as a dilute solution of glyceryl formate, is observed to hydrolyze back into lower substituted esters and its original starting materials such as glycerol and formic acid whereby the efficiency of the solution is diminished. The concentrated solution, such as glyceryl formate, remains at ambient temperatures substantially the same for at least four months, eventually even for a longer period of time.

In one aspect the invention provides a treatment composition which comprises monoester, diester or triester of a water soluble $C_2$-$C_7$ alcohol, more preferably a multivalent, aliphatic water soluble $C_2$-$C_5$ alcohol, such as glycerol, ethylene glycol or propylene glycol, and formic acid or a mixture thereof as an equilibrium solution in order to enhance the applicability of the treatment of wood such as its application and storage properties, such as dimensional stability, reducing cracking, fire resistance and/or inhibiting termites.

According to one preferred embodiment sawn timber, preferably processed sawn timber such as boards, pillars, piles or the like, is treated with a composition which contains glyceryl formate 78-99% by weight, free formic acid 1-20% by weight, the remainder being glycerol and water. When impregnated with this composition a good dimensional stability and reduced cracking were obtained for the processed wood product and the classification of the product in wood protection class 2 was obtained. Moreover the composition used provided the sawn timber also with good protection against termites and decaying agents. The timber thus processed can preferably be used in fences, pillars, piles and for demanding targets in outdoor furniture and yard building applications.

According to a further preferred embodiment sawn timber, preferably processed sawn timber, such as boards, pillars, piles or the like, are treated with a composition, which is a diluted solution obtained from a strong concentrate, that contains 1-30% by weight glyceryl formate, free formic acid 0.1-5.0% by weight, the remainder being glycerol and water. The wood product thus treated can preferably be used for building outdoor furniture.

The invention provides also a wood product treated according to the treatment composition and method described above. The functioning of the treatment composition according to the invention is thought to be based on chemically modifying, formylating, wood with a formic acid ester, however, without the latter being bound thereto. Formate, for instance as a salt, typically merely fills cell cavities without, however, modifying the chemical structure of the cell walls of wood material. Glyceryl formate, in turn, can substitute hydroxyl groups in the wood structure via transesterification by thus forming into the wood structure e.g. cellulose formate i.e. formic acid cellulose. Formylating the wood structure enhances its durability and dimensional stability as well as increases the hydrophobic nature of the structure. Due to its modified chemical composition, formylated wood is in comparison to native wood less well suited as nourishment of microbes. In addition to this, increasing hydrophobicity of wood means less moisture in its structure which in part inhibits microbial growth. Formylation of the wood structure has a harmful effect even to functioning of insects, such as termites, that use wood as nourishment thereby inhibiting damage caused by insects to the wood product.

Used alone or together carboxylic acids and/or salt derivatives thereof don't accomplish significant formylation of the wood product nor do they accomplish high and permanent formate content in the wood product after use and thus as efficient longterm protection as the wood product treated with ester solution of formic acid.

With the term "free formate" is meant formate present in the wood structure that washes out of the structure as the wood is sufficiently extracted with water. Free formate is thus formate that is not bound to the structure of wood, such as e.g. cellulose, but exists as free species in the cells of wood structure. Free formate doesn't change the chemical structure of wood.

Before long, the free formate that is in salt form is leached out of the wood structure, especially in a long-term exposure to moisture or water. Thereby the good properties achieved by the treatment of the wood product are gradually lost with time, and additionally salting out of the surface might occur, while this is generally regarded as an aesthetical disadvantage but it can also make the surface treatment more difficult. Free formate in salt form increases even the hygroscopicity of wood, depending on the amount conveyed thereto. Hygroscopic qualities of wood may increase the risk for decay, and the extra water present in the wood might diminish the durability properties of wood.

With the term "formate bound to the structure" is meant formate that is not washed out of the structure of the wood product when extracting it with water. It is a well-known fact that by treating with formic acid in the chemical modification of cellulose the hydroxyl groups are esterified to cellulose formate. As described in application FI85510, in order to release the bound formate out of the structure of the wood product it must be separately treated with a base, e.g. NaOH. When for instance cellulose formate is treated with the base sodium hydroxide, water soluble sodium formate is produced of its formyl group as a result of the hydrolyzation reaction.

When formate groups are bound to the structure of wood its chemical structure is modified. Water as such is not capable substantially hydrolyzing the formyl groups, even during a longer period of time, as happens with acetyl groups. Therefore the formate bound to the structure is not freed nor is formic acid essentially formed in the wood upon exposure to moisture. Formylation is a long-term solution for enhancing the dimensional stability and durability against decay of wood, even under challenging weather conditions. The changes to wood caused by moisture are lessened and the hydrophobic nature of wood is emphasized, which in turn decreases risk of decay. Also, surface treatment of wood that is more stable, is easier. Formylation is a stronger reaction than acetylation and as a result the hydroxyl groups of the wood structure can be more efficiently reacted compared to acetylation.

The impregnated wood product according to claim 11 contains at least 0.1% by weight of formate, preferably at least 0.5% by weight, most preferred at least 0.8% by weight, such as 0.9% by weight, bound into the structure of the wood product, Accordingly, this is the amount of formate bound to the wood material. The formate is not washed out of the structure when extracting it with water, which is typical to the point of use, where it is especially the water and moisture in the surroundings that cause together with the carbohydrates contained in wood a favourable environment for microbial growth. In order to substantially decrease the formate content of wood the wood product should be treated with a base which, however, would constitute a rare natural environment for usage of treated wood product.

The amount of formate bound into the structure can be determined by measuring the total amount of formate in the wood product by well-known means, such as using sodium hydroxide, preferably 0.5 M NaOH, in extracting the wood product, and measuring the amount of free formate in well-known ways, such as by using extracting with water and subtracting the amount of free formate from total formate content.

According to a preferred embodiment formic acid esters of the structure components of wood, preferably cellulose formate, hemicellulose formate, lignine formate or mixtures thereof are present in the wood product treated with the method according to the invention and treating composition. The modification, formylation, of the structure of the treated wood product may be observed by the composition of the treated wood product in well-known ways, e.g. by spectroscopic means, preferably IR (infra-red) or $^{13}$C-NMR (nuclear magnetic resonance spectroscopy), or by titrating with a base as stated above. In the IR-spectrum measured from a wood product treated according to the invention one can notice absorption bands characteristic for the formic acid esters of wood structure components at wavelengths 1700-1800 cm$^{-1}$ caused by esterification of the hydroxyl groups of the wood structure in formylation and the differences in C/O/H bonds caused by the formic ester groups thus formed. When comparing an IR-spectrum measured from untreated wood product that contains hydroxyl groups to a wood product treated with the treatment composition according to the invention, distinct additional absorptions appear the intensities of which are preferably more than double-fold, at wavelengths 1700-1800 cm$^{-1}$.

From the wood product treated with the treatment composition even the relative substitution level of hydroxyl groups can be measured from the $^{13}$C-NMR-spectrum of the carbon rings in the structure and thus determine the concentration of formate bound into the wood product. The amount of formate ester formed in the treated wood product depends on the treating solution, amounts of glyceryl formate, formic acid and water and optional additives plus the treatment temperature. It is preferred that the amount of formate esters in the wood product treated is more than 0.1% by weight, more preferably more than 0.15% by weight of dry matter in the wood product.

The wood product treated according to the inventive method and treatment composition has a high formate content i.e. the high amount of formate bound into the structure produces for the wood product treated a good, long-term dimensional stability and biological resistance that amounts to a long-term ability to resist the impact of moulds, decaying and blue stain fungi in various environmental conditions. A high concentration of formate lessens also the tendency of the wood product treated to cracking and changes in colour and increases its hydrophobicity. The high formate content of the wood product treated also improves the fire resistance of wood and the ability thereof to sustain attacks by termites.

In the literature, results have been presented of the improvement of resistance to termites of acetylated wood compared to untreated wood. Similarly for formate treated wood at least as good, preferably even better qualities, are obtained, i.e. formylation as a treatment is even more efficient against termites, because of the incompatibility of formylated wood as nourishment for termites.

The invention provides in one aspect also a composition for treating wood the essential component of which is an equilibrium solution of glyceryl formate either as concentrated or diluted form, and in addition thereto a chelating agent and/or hydrophobicity increasing agent with which especially good endurance and protective qualities are obtained against various effects due to the environment of use. Additionally the composition may contain also a biocide and/or colouring agent.

According to another embodiment of the invention the composition for treating wood comprises an equilibrium solution of glyceryl formate that consists of 1-99% by weight glyceryl formate, free formic acid, glycerol and water and hydrophobicity increasing agent, preferably alkylketenedimer (AKD).

According to one preferred embodiment the composition comprises glyceryl formate 78-99% by weight, free formic acid 1-20% by weight, 0.1-5.0% by weight AKD, the balance being glycerol and water. More preferably the composition comprises glyceryl formate 78-89% by weight, free formic acid 5-15% by weight, 0.1-2.0% by weight AKD, the balance being glycerol and water. By impregnating with this solution the amount of water absorbed into the wood is decreased by several percents compared to untreated wood whereby an improvement is achieved further in the dimensional stability and resistance to decay. This kind of product is well suited for demanding building of structures in the yard and in the garden where a special, water repellent wax surface, or foil, is desired for surfaces.

According to another preferred embodiment the composition for treating wood comprises glyceryl formate 1-50% by weight, free formic acid 0.1-20% by weight, 0.1-5.0% by weight AKD, the balance being glycerol and water. More preferably the composition comprises glyceryl formate 1-30% by weight, free formic acid 5-15% by weight, 0.1-2.0% by weight AKD, the balance being glycerol and water.

According to a further embodiment of the present invention the composition for treating wood comprises an equilibrium solution of glyceryl formate, that comprises 1-99% by weight glyceryl formate, free formic acid, glycerol and water and as a hydrophobicity increasing agent polyethene or a derivative thereof; such as oxidized polyethene.

According to another preferred embodiment the composition for treating wood comprises glyceryl formate 78-89% by weight, free formic acid 0.1-20% by weight, 0.1-20% by weight polyethene or oxidized polyethene, the balance being glycerol and water. More preferably the composition comprises glyceryl formate 78-89% by weight, free formic acid 0.1-10% by weight, 0.1-10% by weight polyethene or oxidized polyethene, the balance being glycerol and water.

According to another preferred embodiment the composition for treating wood comprises glyceryl formate, free formic acid 0.1-20% by weight, 0.1-20% by weight polyethene or oxidized polyethene, the balance being glycerol and water. More preferably the composition comprises glyceryl formate 1-30% by weight, free formic acid 0.1-10% by weight, 0.1-10% by weight polyethene or oxidized polyethene, the balance being glycerol and water.

According to one embodiment of the invention the composition for treating wood comprises an equilibrium solution of glyceryl formate that comprises 1-99% by weight glyceryl formate, free formic acid, glycerol and water, plus a chelating agent, preferably a biodegradable chelating agent, more preferably phosphonic acid or a salt thereof, such as 1-hydroxy-ethylidene-1,1-diphosphonic acid (HEDP) or a derivative of aspartic acid, such as N-bis42-(1,2-dicarboxy ethylidene-1,1-diphosphonic acid (HEDP), or a derivative of aspartic acid, such as N-bis-[2-(1,2-dicarboxy etoxy)ethyl]aspartic acid (AES).

According to one preferred embodiment the composition for treating wood comprises glyceryl formate 1-50% by weight, free formic acid 0.1-10% by weight, 20-50% by weight HEDP, the balance being glycerol and water. More preferably the composition comprises glyceryl formate 1-30% by weight, free formic acid 0.1-5% by weight, 0.1-20% by weight HEDP or AES and/or a salt thereof, the balance being glycerol and water.

According to one preferred embodiment of the invention the composition for treating wood comprises a balanced solution of glyceryl formate, that contains 1-99% by weight glyceryl formate, free formic acid, glycerol and water, plus a chelating agent, preferably a substantially biodegradable chelating agent, more preferably phosphonic acid or a salt thereof, such as 1-hydroxy-ethylidene 1,1-diphosphonic acid (HEDP) or a derivative of aspartic acid, such as N-bis-[2-(1,2-dicarboxy ethoxy)ethyl]aspartic acid (AES), hydrophobicity increasing agent, preferably alkyl ketene dimer (AKD) or polyethene or a derivative thereof, such as oxidized polyethene.

According to one preferred embodiment the composition for treating wood comprises glyceryl formate 1-50% by weight, free formic acid 1-10% by weight, 1-50% by weight HEPD or a salt thereof, the balance being glycerol and water. More preferably the composition comprises glyceryl formate 1-30% by weight, free formic acid 0.1-5% by weight, 20-50% by weight ethene, the balance being glycerol and water. By impregnation with this solution a wood product is obtained the fire resistance class of which is the highest possible and that is very durable against decaying agents and termites. In addition, the surface of this product is especially water repellent.

According to a further preferred embodiment the composition for treating wood comprises a balanced solution of glyceryl formate, that comprises 1-99% by weight glyceryl formate, free formic acid, glycerol and water, plus hydrophobicity increasing agent, preferably alkyl ketene dimer (AKD) or polyethene or oxidized polyethene, and/or a chelating agent, preferably substantially biodegradable chelating agent, more preferably phosphonic acid or a salt thereof, such as 1-hydroxy-ethylidene-1,1-diphosphonic acid (HEDP) and additionally an organic biocide, preferably iodopropan-2-yl N-butyl carbamate (IPBC), and/or a colouring agent. More preferably the composition contains glyceryl formate 1-50% by weight, free formic acid 1-10% by weight, 0.1-5% by weight AKD or polyethene or oxidized polyethene, 1-50% by weight HEDP or a salt thereof and IBPC 0.1-5% by weight, and/or a colouring agent 0.1-10% by weight, the balance being glycerol and water. More preferably the composition comprises glyceryl formate 1-30% by weight, free formic acid 0.1-5% by weight, 0.1-2% by weight AKD or polyethene or oxidized polyethene, 20-50% by weight HEDP or a salt thereof and IPBC 0.1-2% by weight, and/or a colouring agent 0.1-5% by weight, the balance being glycerol and water. The thus treated wood product, the colour of which is as desired, is resistant against decaying agents and termites and it belongs to the highest fire resistance class B.

In the following examples the invention is described in more detail. The examples are intended as illustrative only and they are not to be construed as limiting the invention.

EXAMPLE 1

A reactor made of glass is charged with 220 ml (3.0 mol) glycerol at a temperature of 25° C. 497 ml (13.05 mol) of formic acid, the concentration of which is 99%, is slowly added thereto. After the addition of formic acid is completed, the temperature in the reactor is raised until the water that is formed in the esterification reaction begins to distil off together with the formic acid. The distillation is continued until the temperature in the reactor reaches about 140° C. The content of the reactor is cooled down after which the product is collected.

According to the NMR (nuclear magnetic resonance) analysis the glyceryl formate composition obtained comprises 14.9% by weight monoesters of glycerol, 47.5% by weight diesters and 19.1% by weight of triester as well as 1.3% by weight free glycerol and 14.9% by weight formic acid.

According to a KF (Karl Fisher) analysis the product further contains 2.4% by weight water. The substitution level of glycerol is 1.9 as calculated on the basis of the result of the analysis.

EXAMPLE 2

A series of experiments is carried out wherein the influence of the moisture of the surroundings on the wood material treated is simulated acceleratedly:

The wood samples (pine: 25 mm×50 mm×15 mm) A-D are predried over night at the temperature of 105° C., after which they are allowed to cool and they are weighted. After predrying each sample is immersed in 400 ml of the treatment composition for two days at room temperature. After the treatment the samples are after-dried at the temperature of 105° C. over night.

Each dried wood sample is immersed into 400 ml of ion exchanged water at room temperature and the formate concentration of each sample is followed for 11 days. After this, the samples are further dried at the temperature of 105° C. over night and they are weighted.

For the dried samples the concentrations of free formate and the concentrations of formate attached into the structure are determined with liquid chromatography (LC) in a well-known manner.

The concentration of free formate is analyzed for each sample by extracting the wood sample with water, and for each sample the combined concentration of the formate bound into the structure and of free formate is analyzed by extracting the samples with 0.5 M water solution of sodium hydroxide. The concentration of the formate bound into the structure is calculated by subtracting the amount of free formate from the combined concentration.

The treatment solutions used:
A—5% by weight water solution of calcium formate (Kemira)
B—5% by weight water solution of calcium formate containing 1% by weight silicone containing hydrophobicity of the wood material enhancing agent (Wacker HC 303)
C—5% by weight water solution of glyceryl formate (a diluted product mix prepared according to example 1)
D—a solution of glyceryl formate (a concentrated product mix prepared according to example 1)

From Table 1 can be seen the change in weight of samples A-D caused by the treatment compared to the weight of the original, untreated sample and the change in weight due to the extraction by sodium hydroxide after the treatment.

TABLE 1

| Sample | Untreated | Treated | Extracted |
|--------|-----------|---------|-----------|
| A | 10.2150 | 10.3397 | 10.1082 |
| B | 10.3370 | 10.4645 | 10.1715 |
| C | 10.5164 | 10.5913 | 10.3581 |
| D | 9.2855 | 10.4985 | 9.279 |

When using the concentrated solution D of glyceryl formate a substantially larger amount of formate can be driven into the structure of the wood sample than when using the other treatment solutions. After the extraction the change in weight of the sample treated with concentrated glyceryl formate compared to the weight of the original sample is much smaller compared to the samples treated with the other treatment solutions.

As end result the obtained amounts of formate bound into the structure of wood treated in the accelerated experiment simulating the effect of the moisture in the surroundings are presented in Table 2. When using diluted glyceryl formate solution the amount of formate which is not extracted into water but remains in the structure is 2 to 6 fold compared to a treatment solution not containing glyceryl formate. In the case of concentrated glyceryl formate the amount is larger even by one decade.

TABLE 2

| Sample | Total amount of formate (% by weight) | Amount of free formate (% by weight) | Amount of bound formate (% by weight) |
|--------|---------------------------------------|--------------------------------------|---------------------------------------|
| A | 0.13 | 0.10 | 0.03 |
| B | 0.15 | 0.07 | 0.08 |
| C | 0.23 | 0.04 | 0.19 |
| D | 1.09 | 0.20 | 0.89 |

According to the results in the treatment with glyceryl formate the formate bound into the structure of wood endures excellently the effect of moisture in the surroundings, giving thus a long-term protective effect to the wood.

EXAMPLE 3

The formate bound as ester into the structure of wood may be qualitatively determined by measuring the IR spectrum of the surface of a slice cut from the treated wood sample. In the spectrum a strong absorbance in the region 1700-1800 $cm^{-1}$ typical for an ester structure may be seen.

A quantitative assessment of the formate bound into the structure of wood is obtained with the extraction method described above in example 2 and by liquid chromatography (LC) analysis. The amount of formate bound into the structure of a wood product is determined by measuring the total amount of formate in the wood product by using in the extraction of the wood product 0.5 M sodium hydroxide and by measuring the amount of free formate by using extraction with water and then subtracting from the total amount of formate obtained the amount of free formate.

The invention claimed is:

1. A method for treating wood for esterification of said wood characterized in that said wood to be treated is contacted with a treatment composition which comprises 1 to 30% by weight of glyceryl formate, wherein said glyceryl formate is formed by glycerol and formic acid as an equilibrium solution in water and wherein said treatment composition is used in a concentration of 1 to 100% by weight.

2. The method according to claim 1, wherein said treatment composition is used in a concentration of 1 to 50% by weight.

3. The method according to claim 1, characterized in that said wood to be treated comprises harvested or processed raw wood suitable for construction material.

4. The method according to claim 1, characterized in that said treatment composition is contacted with said wood by impregnating.

5. The method according to claim 1, characterized in that the method comprises at least the following stages:
   the wood to be treated is first dried at a temperature 10-110° C. at a reduced pressure;
   the composition is contacted with the wood at an elevated temperature and at an elevated pressure; and
   the wood treated is dried at an elevated temperature and at a reduced pressure.

6. The method according to claim 5, wherein the wood treated is dried at an elevated temperature of about 90 to 110 ° C.

7. The method according to claim 5, wherein the wood treated is characterized in that said wood comprises formate at least 0.1% by weight, when measured from wood dry matter and as formate bound into the structure of wood in a way that it cannot be washed out of said structure when extracting with water.

8. The method according to claim 5, wherein the wood treated is characterized in that said wood comprises formate at least 0.8% by weight, when measured from wood dry matter and as formate bound into the structure of wood in a way that it cannot be washed out of said structure when extracting with water.

9. The method according to claim 1, wherein said wood comprises at least one of harvested wood suitable for construction material or processed raw wood suitable for construction material.

10. The method according to claim 1, wherein said wood comprises at least one of sawn timber or refined wood products derived from sawn timber.

11. The method according to claim 1, wherein said treatment composition is applied to said wood by at least one of: pressure treatment impregnation, submerging, spraying, vaporization, atomization or application.

12. The method according to claim 1, wherein said treatment composition is used in a concentration of 1 to 30% by weight.

13. The method according to claim 1, further comprising a chelating agent.

14. The method according to claim 13, wherein the chelating agent a biodegradable chelating agent.

15. The method according to claim 13, wherein the chelating agent is selected from the group consisting of: phosphonic acid or a salt thereof and a derivative of aspartic acid.

16. The method according to claim 13, wherein the chelating agent is selected from the group consisting of: 1-hydroxyethylidene-1,1-diphosphonic acid (HEDP) and N-bis-[2-(1,2-dicarboxyetoxy)ethyl] aspartic acid (AES).

17. The method according to claim 1, further comprising a hydrophobicity rendering agent.

18. The method according to claim 17, wherein the hydrophobicity rendering agent is an alkylkentenedimer (AKD) or polyethene or a derivative thereof.

19. The method according to claim 1, further comprising an agent protective against mould.

20. The method according to claim 1, further comprising a colouring agent.

* * * * *

UNITED STATES PATENT AND TRADEMARK OFFICE
CERTIFICATE OF CORRECTION

| | | |
|---|---|---|
| PATENT NO. | : 9,125,404 B2 | Page 1 of 1 |
| APPLICATION NO. | : 13/381280 | |
| DATED | : September 8, 2015 | |
| INVENTOR(S) | : Vuori et al. | |

It is certified that error appears in the above-identified patent and that said Letters Patent is hereby corrected as shown below:

Title Page, item (73) should read: TAMINCO FINLAND

Signed and Sealed this
Tenth Day of November, 2015

Michelle K. Lee
*Director of the United States Patent and Trademark Office*